United States Patent
Zaima et al.

(10) Patent No.: US 10,117,876 B2
(45) Date of Patent: Nov. 6, 2018

(54) PHARMACEUTICAL COMPOSITION OF FUSED AMINODIHYDROTHIAZINE DERIVATIVE

(71) Applicant: Eisai R&D Management Co., Ltd., Tokyo (JP)

(72) Inventors: Yasuhiro Zaima, Gifu (JP); Kazuo Kazama, Gifu (JP); Shuntaro Arase, Gifu (JP); Kentaro Nagane, Gifu (JP); Kanta Horie, Gifu (JP); Yosuke Ueki, Gifu (JP)

(73) Assignee: Eisai R&D Management Co., Ltd., Tokyo (JP)

(*) Notice: Subject to any disclaimer, the term of this patent is extended or adjusted under 35 U.S.C. 154(b) by 31 days.

(21) Appl. No.: 15/516,567

(22) PCT Filed: Oct. 8, 2015

(86) PCT No.: PCT/JP2015/078688
§ 371 (c)(1),
(2) Date: Apr. 3, 2017

(87) PCT Pub. No.: WO2016/056638
PCT Pub. Date: Apr. 14, 2016

(65) Prior Publication Data
US 2018/0263998 A1 Sep. 20, 2018

(30) Foreign Application Priority Data
Oct. 10, 2014 (JP) .................. 2014-209289

(51) Int. Cl.
*A61K 31/542* (2006.01)
*C07D 513/04* (2006.01)
*A61K 9/20* (2006.01)

(52) U.S. Cl.
CPC .......... *A61K 31/542* (2013.01); *A61K 9/2018* (2013.01); *A61K 9/2054* (2013.01)

(58) Field of Classification Search
CPC .................... A61K 31/542; C07D 513/04
USPC ............................ 514/224.2; 544/48
See application file for complete search history.

(56) References Cited

U.S. PATENT DOCUMENTS

| 8,158,620 | B2 | 4/2012 | Suzuki et al. |
| 2012/0094984 | A1 | 4/2012 | Suzuki et al. |
| 2014/0271911 | A1 | 9/2014 | Wallace |

FOREIGN PATENT DOCUMENTS

| EP | 2233474 | 9/2010 |
| WO | WO 2009/091016 | 7/2009 |

OTHER PUBLICATIONS

Japan Pharmaceutical Excipients Council, revised edition, Handbook of Pharmaceutical Excipients, Yakuji Nippo Ltd., 1 Banch, Kanda 2007, ISBN978-4-8408-0968-9, p. 465, 468, 471, 462, 1007.

Takahashi et al., "Effects of Physicochemical Properties of Lubricants on Drug Release from Tablets," Annual Meeting of Pharmaceutical Society of Japan, 2012, p. 169 #30E17-pm02S.
[No Author Listed] "History of Changes for Study: NCT01716897. An Study to Determine the Bioavailability of E2609 Tablets Compared to Capsules and the Effect of Food on Absorption," ClinicalTrials. gov, 5 pages (May 20, 2013).
[No Author Listed] "History of Changes for Study: NCT02222324. A Study to Evaluate the Effects of E2609 on QTc Interval in Healthy Subjects," ClinicalTrials.gov, 6 pages (Nov. 2, 2015).
International Preliminary Report on Patentability in International Application No. PCT/JP2015/078688, dated Apr. 11, 2017, 10 pages (English Translation).
International Search Report in International Application No. PCT/JP2015/078688, dated Nov. 10, 2015, 2 pages (English Translation).
Kibbe et al., Handbook of Pharmaceutiocal Excipients, p. 305, 276, 102, 528, 87, 433 (Jan. 1, 2000).
Office Action in Singapore Patent Application No. 11201702632Q, dated Jan. 12, 2018, 7 pages (English Translation).
Response to Office Action in Singapore Patent Application No. 11201702632Q, filed on Jun. 13, 2018, 9 pages (English Translation).
Supplementary European Search Report in European Patent Application No. 15848771.0, dated May 8, 2018, 8 pages.
Hiroaki Okada, et al, Passing of Formulation Skills of Formulation Experts, 2013, p. 151, (7 pages with English Translation).
Japan Pharmaceutical Excipients Council, revised edition, Handbook of Pharmaceutical Excipients, Yakuji Nippo Ltd., 1 Banch, Kanda 2007, ISBN978-4-8408-0968-9, P156, P465, 468, 471, 762, 1007, (21 pages with English translation).
Notice of Reasons for Rejection dated Aug. 31, 2018 for JP Appln No. 2016-553160, (12 pages with English translation).

*Primary Examiner* — Brenda L Coleman
(74) *Attorney, Agent, or Firm* — Fish & Richardson P.C.

(57) ABSTRACT

The present invention provides a pharmaceutical composition comprising a compound represented by formula (1):

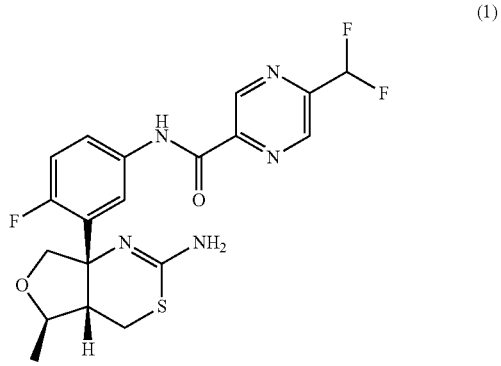

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and a salt of a compound having a C12-22 saturated aliphatic hydrocarbon group.

4 Claims, 6 Drawing Sheets

PHARMACEUTICAL COMPOSITION OF FUSED AMINODIHYDROTHIAZINE DERIVATIVE

TECHNICAL FIELD

The present invention relates to a pharmaceutical composition of a fused aminodihydrothiazine derivative. More particularly, the present invention relates to a pharmaceutical composition comprising a fused aminodihydrothiazine derivative in the form of a compound represented by formula (1):

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing.

BACKGROUND ART

The BACE1 (Beta-site Amyloid Precursor Protein Cleaving Enzyme 1) inhibitor, N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, is a compound having the structure represented by formula (1) (to be simply referred to as "Pharmacological Compound 1").

Pharmacological Compound 1 or a pharmaceutically acceptable salt thereof is expected to be used as a therapeutic agent for dementia and MCI (mild cognitive impairment) (Patent Document 1).

CITATION LIST

Patent Document

Patent Document 1: U.S. Pat. No. 8,158,620 (Specification)

SUMMARY

Technical Problem

The problem to be solved by the present invention is to provide a pharmaceutical composition comprising a compound represented by formula (1), N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, which does not cause a substantial change in the dissolution profile even after storage for a certain period of time.

Solution to Problem

As a result of conducting extensive studies to solve the above-mentioned problem, the inventors of the present invention found that the above-mentioned problem is solved by a pharmaceutical composition comprising a compound represented by formula (1), N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and an additive that does not cause a substantial change in the dissolution profile even after storage for a certain period of time, thereby leading to completion of the present invention.

The present invention is as indicated below.

[1] A pharmaceutical composition comprising a compound represented by formula (1):

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and
a salt of a compound having a C12-22 saturated aliphatic hydrocarbon group.

[2] The pharmaceutical composition described in [1], wherein the salt of a compound having a C12-22 saturated aliphatic hydrocarbon group is at least one selected from the group consisting of a metal salt of a C12-22 saturated aliphatic organic acid, a mono alkaline metal salt of a mono C12-22 alkyl fumarate, and a mono alkaline earth metal salt of a mono C12-22 alkyl fumarate.

[3] The pharmaceutical composition described in [1], wherein the salt of a compound having a C12-22 saturated aliphatic hydrocarbon group is at least one selected from the group consisting of sodium stearyl fumarate, sodium lauryl sulfate, calcium stearate and magnesium stearate.

[4] A pharmaceutical composition comprising a compound represented by formula (1):

(1)

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and means that does not cause a substantial change in the dissolution profile even after storage for a certain period of time.

Advantageous Effects of Invention

According to the present invention, a pharmaceutical composition can be provided that contains a compound represented by formula (1), N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, which does not cause a substantial change in the dissolution profile even after storage for a certain amount of time.

DESCRIPTION OF THE EMBODIMENTS

Hereinafter, the present invention will be described in more detail. Furthermore, the present invention is not limited to the following embodiments, and can be carried out while making various modifications thereto within the range of the gist thereof.

The present invention relates to a pharmaceutical composition comprising a compound represented by formula (1)

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or pharmaceutically acceptable salt of the foregoing, and a salt of a compound having C12-22 saturated aliphatic hydrocarbon group.

A compound represented by formula (1) or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide used in the present invention is described as Compound 43 of WO 2012/100179.

The compound represented by formula (1) or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide may be in the free form or in the form of a pharmaceutically acceptable salt. It is preferably in the free form.

Examples of pharmaceutically acceptable salts include salts of inorganic acids such as sulfates, nitrates, perchlorates, phosphates, carbonates, bicarbonates, hydrofluorides, hydrochlorides, hydrobromides or hydroiodides, salts of organic acids such as acetates, oxalates, maleates, tartrates, fumarates, citrates, methanesulfonates, trifluoromethanesulfonates, ethanesulfonates, benzenesulfonates, toluenesulfonates or camphorsulfonates, amino acid salts such as aspartates or glutamates, quaternary amine salts, and metal salts such as sodium salts, potassium salts, magnesium salts or calcium salts.

Pharmacological Compound 1 or a pharmaceutically acceptable salt thereof can be obtained by the method described in Patent Document 1, a modification thereof, or a method that is obvious to the ordinary skilled in the art.

A salt of a compound having a C12-22 saturated aliphatic hydrocarbon group contained in the pharmaceutical composition according to the present invention refers to a salt composed of a compound having a saturated aliphatic hydrocarbon group having 12 to 22 carbon atoms in a molecule thereof and a functional group having a positive charge or negative charge in a portion thereof other than the C12-22 saturated aliphatic hydrocarbon group, and a counter ion ionically bonded thereto.

A preferable compound can be selected for the salt of a compound having a C12-22 saturated aliphatic hydrocarbon group from the viewpoint of having stability that does not cause a substantial change in the dissolution profile even after storage for a certain period of time. In addition, a preferable compound may also be selected from the viewpoints of enhancing powder fluidity and preventing adhesion of powder with respect to moldability in a solid preparation.

Examples of a salt of a compound having a C12-22 saturated aliphatic hydrocarbon group include quaternary ammonium salts having a C12-22 alkyl group such as cetylpyridinium chloride, metal salts of a C12-22 saturated aliphatic organic acid such as sodium lauryl sulfate or magnesium stearate, mono-C12-22 alkyl monoalkaline metal salts of fumaric acid such as sodium stearyl fumarate, and mono-C12-22 alkyl monoalkaline earth metal salts of fumaric acid such as magnesium stearyl fumarate.

The said salt may be used alone or two or more kinds of salts may be used.

A C12-22 saturated aliphatic organic acid refers to an organic acid having an aliphatic chain having 12 to 22 carbon atoms but not having an unsaturated bond.

The aliphatic chain may be linear or branched. Examples of organic acids include carboxylic acid and sulfuric acid.

A metal salt of a C12-22 saturated aliphatic organic acid refers to a salt in which a metal is bonded to a C12-22 saturated aliphatic organic acid, and examples thereof include alkaline metal salts such as sodium salts or potassium salts, alkaline earth metal salts such as magnesium salts or calcium salts, zinc salts, and aluminum salts.

Examples of alkaline metal salts of C12-22 saturated aliphatic organic acids include potassium lauryl sulfate, sodium lauryl sulfate, sodium myristate, potassium palmitate, potassium stearate and sodium stearate.

Examples of alkaline earth metal salts of C12-22 saturated aliphatic organic acids include magnesium lauryl sulfate, magnesium myristate, calcium palmitate, magnesium stearate and calcium stearate.

Examples of zinc salts and aluminum salts of C12-22 saturated aliphatic organic acids include zinc stearate and aluminum stearate.

A mono alkaline metal salt of a mono C12-22 alkyl fumarate refers to a salt having a fumaric acid monoalkyl ester structure in which one of the two carboxylic acids of fumaric acid is ester-bonded to an alkyl alcohol having 12 to 22 carbon atoms, while the other carboxylic acid is bonded to an alkaline metal.

The alkyl alcohol having 12 to 22 carbon atoms may be a linear alkyl alcohol or branched alkyl alcohol, and examples thereof include lauryl alcohol, myristyl alcohol, palmityl alcohol and stearyl alcohol.

Examples of a mono alkaline metal salt of a mono C12-22 alkyl fumarate include sodium stearyl fumarate, potassium lauryl fumarate and sodium myristyl fumarate.

A mono alkaline earth metal salt of a mono C12-22 alkyl fumarate refers to a salt having a fumaric acid monoalkyl ester structure in which one of the two carboxylic acids of fumaric acid is ester-bonded to an alkyl alcohol having 12 to 22 carbon atoms, while the other carboxylic acid is bonded to the alkaline earth metal.

Examples of a mono alkaline earth metal salt of a mono C12-22 alkyl fumarate include magnesium stearyl fumarate, calcium lauryl fumarate and magnesium palmityl fumarate.

The salt of a compound having a C12-22 saturated aliphatic hydrocarbon group contained in the pharmaceutical composition according to the present invention is preferably sodium stearyl fumarate, sodium lauryl sulfate, calcium stearate or magnesium stearate, and more preferably sodium stearyl fumarate.

The blending ratio of the salt of a compound having a C12-22 saturated aliphatic hydrocarbon group to the total mass of the pharmaceutical composition according to the present invention is normally 0.1% by mass to 10% by mass, preferably 0.2% by mass to 5% by mass, and more preferably 0.3% by mass to 3% by mass.

In the present invention, an "alkaline earth metal" includes beryllium, magnesium, calcium, strontium and barium, and is preferably magnesium or calcium.

The pharmaceutical composition according to the present invention preferably may contain one or more compounds selected from the group of compounds indicated below from the viewpoint of rapid dissolution of Pharmacological Compound 1 or a pharmaceutically acceptable salt thereof.

Examples of these compounds include low-substituted hydroxypropyl cellulose, partially gelatinized starch, starch (such as rice starch, wheat starch, potato starch or cornstarch), crospovidone, carmellose, carmellose calcium, croscarmellose sodium and sodium carboxymethyl starch. Preferable examples of these compounds include low-substituted hydroxypropyl cellulose, starch, crospovidone, carmellose calcium, carmellose and sodium carboxymethyl starch.

The pharmaceutical composition according to the present invention may also contain crystalline cellulose, agar, gelatin, calcium carbonate, sodium bicarbonate, calcium citrate, dextrin or pectin in addition to the previously exemplified compounds.

The pharmaceutical composition according to the present invention has stability that does not cause a substantial change in the dissolution profile of Pharmacological Compound 1 or a pharmaceutically acceptable salt thereof even after storage for a certain period of time.

In the present invention, "not cause a substantial change in the dissolution profile even after storage for a certain period of time" means that change in the dissolution rates in 15 minutes (or 30 minutes) after storage for a certain period of time relative to the initial dissolution rates in 15 minutes (or 30 minutes) prior to storage can fall within ±20%.

Although there are no particular limitations on the dissolution conditions provided they allow dissolution of Pharmacological Compound 1 to be measured, as will be subsequently described in the examples, an dissolution test is preferably carried out in accordance with the dissolution test method described in the 16th edition of the Japanese Pharmacopoeia using 900 mL of a 0.1 mol/L aqueous hydrochloric acid solution adjusted to a temperature of 37° C.±0.5° C. and at a paddle rotation speed of 50 rpm.

In the present invention, a pharmaceutical composition is preferable in which Pharmacological Compound 1 or a pharmaceutically acceptable salt thereof rapidly dissolves even after storage at 60° C. and 75% relative humidity for normally 2 weeks and preferably 1 month under conditions of being open to the atmosphere and under protection from light in the same manner as prior to storage.

In the present invention, "rapidly dissolves" means that an average of dissolution rate is normally 75% or more, preferably 80% or more and more preferably 85% or more.

The average 15 minute dissolution rate after storage for 2 weeks at 60° C. and 75% relative humidity under conditions of being open to the atmosphere and under protection from light is normally 75% or more, preferably 80% or more and more preferably 85% or more. The average 15 minute dissolution rate after storage for 1 month at 60° C. and 75% relative humidity under conditions of being open to the atmosphere and under protection from light is normally 75% or more, preferably 80% or more and more preferably 85% or more. The average 15 minute dissolution rate after storage for 3 months at 40° C. and 75% relative humidity under conditions of being open to the atmosphere and under protection from light is normally 75% or more, preferably 80% or more and more preferably 85% or more. The average 15 minute dissolution rate after storage for 6 months at 40° C. and 75% relative humidity under conditions of being open to the atmosphere and under protection from light is normally 75% or more, preferably 80% or more and more preferably 85% or more.

In the present invention, the daily dosage of Pharmacological Compound 1 or a pharmaceutically acceptable salt thereof is normally 0.1 mg to 1000 mg, preferably 1 mg to 250 mg and more preferably 2 mg to 150 mg.

The blending ratio of Pharmacological Compound 1 or a pharmaceutically acceptable salt thereof to the total mass of the pharmaceutical composition according to the present invention is normally 0.1% by mass to 80% by mass, preferably 0.5% by mass to 60% by mass and more preferably 0.9% by mass to 50% by mass.

The pharmaceutical composition according to the present invention may also contain an excipient, binder, disintegrating agent, lubricant, colorant, corrective, dissolution assistant, antioxidant, emulsifier, absorption promoter, surfactant or coating agent in addition to the salt of a compound having a C12-22 saturated aliphatic hydrocarbon group.

Examples of excipients include lactose, sucrose, glucose, mannitol, sorbitol, dextrin, crystalline cellulose, light silicic anhydride, aluminum silicate, calcium silicate, magnesium aluminate metasilicate and calcium hydrogen phosphate.

Examples of binders include polyvinylpyrrolidone, ethyl cellulose, methyl cellulose, gum Arabic, hydroxypropyl cellulose, hydroxypropyl methyl cellulose, carboxymethyl cellulose sodium and polyvinyl alcohol.

Examples of colorants include iron sesquioxide, yellow iron sesquioxide, carmine, caramel, β-carotene, titanium oxide, talc, sodium riboflavin phosphate and yellow aluminum lake.

Examples of correctives include cocoa powder, peppermint oil and cinnamon powder.

Examples of dissolution assistants include polyethylene glycol, propylene glycol, benzyl benzoate, ethanol, cholesterol, triethanolamine, sodium carbonate, sodium citrate, Polysorbate 80 and nicotinic acid amide.

Examples of antioxidants include ascorbic acid, α-tocopherol, ethoxyquin, dibutylhydroxytoluene and butylhydroxyanisole.

Examples of emulsifiers, absorption promoters and surfactants include stearyltriethanolamine, laurylaminopropionic acid, lecithin, glycerin monostearate, sucrose fatty acid esters and glycerin fatty acid esters.

Examples of coating agents include hypromellose, hydroxypropyl cellulose, methyl cellulose, aminoalkylmethacrylate copolymer E and polyvinyl alcohol.

The pharmaceutical composition according to the present invention may be in the form of an uncoated tablet, coated tablet, orally-disintegrating tablet, chewable tablet, hard capsule, soft capsule, granules, grains or powder. Each of these preparation forms of the pharmaceutical composition can be produced by a method known in the prior art.

In the present invention, granules containing Pharmacological Compound 1 or a pharmaceutically acceptable salt thereof are preferably prepared and then formulated from the viewpoint of moldability. There are no particular limitations on a pharmaceutical composition in the form of granules containing Pharmacological Compound 1 or a pharmaceutically acceptable salt thereof, and can be produced by a known method.

The granules may also contain an excipient, binder, disintegration agent, lubricant, colorant, corrective, dissolution assistant, antioxidant, emulsifier, absorption promoter, surfactant or coating agent as necessary in addition to Pharmacological Compound 1 or a pharmaceutically acceptable salt thereof.

In the case of containing granules, the pharmaceutical composition of the present invention is a pharmaceutical composition containing granules containing a compound represented by formula (1):

(1)

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and a salt of a compound having a C12-22 saturated aliphatic hydrocarbon group.

In addition, due to the superior moldability thereof, the pharmaceutical composition of the present invention is a solid preparation, and more specifically, a tablet such as an uncoated tablet, coated tablet, orally-disintegrating tablet or chewable tablet.

EXAMPLES

Although the following provides a more detailed explanation of the present invention using examples thereof, these examples are only intended to be exemplary, and the present invention is not limited thereto.

Example 1

2500 mg of Pharmacological Compound 1, 2285 mg of lactose (DFE Pharma), 330 mg of low-substituted hydroxypropyl cellulose (LH21, Shin-Etsu Chemical Co., Ltd.) and 165 mg of hydroxypropyl cellulose (SL, Nippon Soda Co., Ltd.) were mixed in a mortar. A suitable amount of aqueous ethanol solution (30 w/w %) was added to the resulting mixture followed by subjecting to wet granulation in the mortar. After drying the resulting granules using a constant temperature bath, the granules were sized using a sieve having openings of 1 mm.

33 mg of low-substituted hydroxypropyl cellulose (LH21, Shin-Etsu Chemical Co., Ltd.) and 11 mg of sodium stearyl fumarate (JRS Pharma) were added per 1056 mg of sized granules and mixed in a vial. The resulting mixture was compressed at 9 kN using a single-punch tableting machine to obtain tablets having a diameter of 6.5 mm and mass of 110 mg.

Examples 2 to 18 and Comparative Examples 1 to 5

Tablets having a diameter of 6.5 mm and mass of 110 mg were obtained using the same method as Example 1 so as to have the formulations indicated in Tables 1 to 4.

Tables 1 to 4 indicate the constituent amounts of each component per tablet. In addition, each of the components used are as indicated below.

Sodium lauryl sulfate (Nikko Chemicals Co., Ltd.), calcium stearate (Merck KGaA), magnesium stearate (Mallinckrodt plc), stearic acid (Mallinckrodt plc), sucrose fatty acid ester (J-1811F, Mitsubishi-Kagaku Foods Corporation), partially gelatinized starch (Asahi Kasei Chemicals Corp.), cornstarch (Nihon Shokuhin Kako Co., Ltd.), crospovidone (XL-10, ISP), carmellose calcium (Gotoku Chemical Company Ltd.), croscarmellose sodium (FMC), sodium carboxymethyl starch (JRS Pharma), carmellose (Gotoku Chemical Company Ltd.).

TABLE 1

| | Component | Example 1 | Example 2 | Example 3 | Example 4 | Comp. Ex. 1 | Comp. Ex. 2 |
|---|---|---|---|---|---|---|---|
| Inside Granules | Pharmacological Compound 1 | 50.0 mg | 50.0 mg | 50.0 mg | 50.0 mg | 50.0 mg | 50.0 mg |
| | Lactose | 45.7 mg | 45.7 mg | 45.7 mg | 45.7 mg | 45.7 mg | 45.7 mg |
| | Low-substituted hydroxypropyl cellulose | 6.6 mg | 6.6 mg | 6.6 mg | 6.6 mg | 6.6 mg | 6.6 mg |
| | Hydroxypropyl cellulose | 3.3 mg | 3.3 mg | 3.3 mg | 3.3 mg | 3.3 mg | 3.3 mg |
| Outside Granules | Low-substituted hydroxypropyl cellulose | 3.3 mg | 3.3 mg | 3.3 mg | 3.3 mg | 3.3 mg | 3.3 mg |
| | Sodium stearyl fumarate | 1.1 mg | — | — | — | — | — |
| | Sodium lauryl sulfate | — | 1.1 mg | — | — | — | — |
| | Calcium stearate | — | — | 1.1 mg | — | — | — |
| | Magnesium stearate | — | — | — | 1.1 mg | — | — |
| | Stearic acid | — | — | — | — | 1.1 mg | — |
| | Sucrose fatty acid ester | — | — | — | — | — | 1.1 mg |
| | Total | 110 mg | 110 mg | 110 mg | 110 mg | 110 mg | 110 mg |

TABLE 2

| | Component | Example 5 | Example 6 | Example 7 | Example 8 | Example 9 | Example 10 | Example 11 |
|---|---|---|---|---|---|---|---|---|
| Inside Granules | Pharmacological Compound 1 | 50.0 mg | 50.0 mg | 50.0 mg | 50.0 mg | 50.0 mg | 50.0 mg | 50.0 mg |
| | Lactose | 45.7 mg | 45.7 mg | 45.7 mg | 45.7 mg | 45.7 mg | 45.7 mg | 45.7 mg |
| | Partially gelatinized starch | 6.6 mg | — | — | — | — | — | — |

TABLE 2-continued

| | Component | Example 5 | Example 6 | Example 7 | Example 8 | Example 9 | Example 10 | Example 11 |
|---|---|---|---|---|---|---|---|---|
| | Cornstarch | — | 6.6 mg | — | — | — | — | — |
| | Crospovidone | — | — | 6.6 mg | — | — | — | — |
| | Carmellose calcium | — | — | — | 6.6 mg | — | — | — |
| | Croscarmellose sodium | — | — | — | — | 6.6 mg | — | — |
| | Sodium carboxymethyl starch | — | — | — | — | — | 6.6 mg | — |
| | Carmellose | — | — | — | — | — | — | 6.6 mg |
| | Hydroxypropyl cellulose | 3.3 mg | 3.3 mg | 3.3 mg | 3.3 mg | 3.3 mg | 3.3 mg | 3.3 mg |
| Outside | Partially gelatinized starch | 3.3 mg | — | — | — | — | — | — |
| Granules | Cornstarch | — | 3.3 mg | — | — | — | — | — |
| | Crospovidone | — | — | 3.3 mg | — | — | — | — |
| | Carmellose calcium | — | — | — | 3.3 mg | — | — | — |
| | Croscarmellose sodium | — | — | — | — | 3.3 mg | — | — |
| | Sodium carboxymethyl starch | — | — | — | — | — | 3.3 mg | — |
| | Carmellose | — | — | — | — | — | — | 3.3 mg |
| | Sodium stearyl fumarate | 1.1 mg | 1.1 mg | 1.1 mg | 1.1 mg | 1.1 mg | 1.1 mg | 1.1 mg |
| | Total | 110 mg | 110 mg | 110 mg | 110 mg | 110 mg | 110 mg | 110 mg |

TABLE 3

| | Component | Example 12 | Example 13 | Example 14 | Example 15 | Example 16 | Example 17 | Example 18 |
|---|---|---|---|---|---|---|---|---|
| Inside | Pharmacological Compound 1 | 50.0 mg | 50.0 mg | 50.0 mg | 50.0 mg | 50.0 mg | 50.0 mg | 50.0 mg |
| Granules | Lactose | 45.7 mg | 45.7 mg | 45.7 mg | 45.7 mg | 45.7 mg | 45.7 mg | 45.7 mg |
| | Partially gelatinized starch | 6.6 mg | — | — | — | — | — | — |
| | Cornstarch | — | 6.6 mg | — | — | — | — | — |
| | Crospovidone | — | — | 6.6 mg | — | — | — | — |
| | Carmellose calcium | — | — | — | 6.6 mg | — | — | — |
| | Croscarmellose sodium | — | — | — | — | 6.6 mg | — | — |
| | Sodium carboxymethyl starch | — | — | — | — | — | 6.6 mg | — |
| | Carmellose | — | — | — | — | — | — | 6.6 mg |
| | Hydroxypropyl cellulose | 3.3 mg | 3.3 mg | 3.3 mg | 3.3 mg | 3.3 mg | 3.3 mg | 3.3 mg |
| Outside | Partially gelatinized starch | 3.3 mg | — | — | — | — | — | — |
| Granules | Cornstarch | — | 3.3 mg | — | — | — | — | — |
| | Crospovidone | — | — | 3.3 mg | — | — | — | — |
| | Carmellose calcium | — | — | — | 3.3 mg | — | — | — |
| | Croscarmellose sodium | — | — | — | — | 3.3 mg | — | — |
| | Sodium carboxymethyl starch | — | — | — | — | — | 3.3 mg | — |
| | Carmellose | — | — | — | — | — | — | 3.3 mg |
| | Magnesium stearate | 1.1 mg | 1.1 mg | 1.1 mg | 1.1 mg | 1.1 mg | 1.1 mg | 1.1 mg |
| | Total | 110 mg | 110 mg | 110 mg | 110 mg | 110 mg | 110 mg | 110 mg |

TABLE 4

| | Component | Comp. Ex. 3 | Comp. Ex. 4 | Comp. Ex. 5 |
|---|---|---|---|---|
| Inside | Pharmacological Compound 1 | 50.0 mg | 50.0 mg | 50.0 mg |
| Granules | Lactose | 45.7 mg | 45.7 mg | 45.7 mg |
| | Carmellose calcium | 6.6 mg | — | — |
| | Sodium carboxymethyl starch | — | 6.6 mg | — |
| | Carmellose | — | — | 6.6 mg |
| | Hydroxypropyl cellulose | 3.3 mg | 3.3 mg | 3.3 mg |
| Outside | Carmellose calcium | 3.3 mg | — | — |
| Granules | Sodium carboxymethyl starch | — | 3.3 mg | — |
| | Carmellose | — | — | 3.3 mg |
| | Sucrose fatty acid ester | 1.1 mg | 1.1 mg | 1.1 mg |
| | Total | 110 mg | 110 mg | 110 mg |

[Dissolution Test Method]

A dissolution test was carried out in accordance with the dissolution test method described in the 16th edition of the Japanese Pharmacopoeia using 900 mL of a 0.1 mol/L aqueous hydrochloric acid solution adjusted to a temperature of 37° C.±0.5° C. at a paddle rotation speed of 50 rpm. A solution obtained by dissolving Pharmacological Compound 1 in 0.1 mol/L aqueous hydrochloric acid solution was used for the standard solution used to calculate dissolution rate. The standard solution was prepared so that the concentration of Pharmacological Compound 1 was in the vicinity of a concentration equivalent to a dissolution rate of 100%. Measurement specimens were collected from the vessel of the dissolution tester at the specified time after the start of the test and then filtered using a filter having a pore diameter of 0.45 μm.

Dissolution rate was evaluated using the absorbance measurement method or high-performance liquid chromatography method indicated below.

(Absorbance Measurement Method)

Absorbance was measured using a cell having an optical path length of 10 mm under conditions of a measurement wavelength of 300 nm and reference wavelength of 650 nm. Dissolution rate was calculated based on the results of absorbance measurement and the concentration of the prepared standard solution.

(High-Performance Liquid Chromatography Method)

Measurement by high-performance liquid chromatography was carried out under the test conditions indicated below. Dissolution rate was calculated based on the area of the peak corresponding to Pharmacological Compound 1 and the concentration of the prepared standard solution.

Analytical column: Column having inner diameter of 4.6 mm and length of 150 mm packed with 5 μm octadecylsilylated silica gel (Mightysil RP18-GP, Kanto Chemical Co., Inc.) Column temperature: 40° C.

Specimen temperature: 25° C.

Injection volume: 50 μL

Flow rate: Approx. 1 mL/min

Mobile phase: Mixture of water, methanol, 70% perchloric acid and sodium perchlorate monohydrate at a ratio of 600/400/1/7 (v/v/v/w).

Detection wavelength: 270 nm

[Dissolution Test Result 1]

The specimens prepared in Examples 1 to 18 and Comparative Examples 1 to 5 were placed in vials and stored for 2 weeks and 1 month at 60° C. and 75% relative humidity under conditions of being open to the atmosphere and under protection from light. The dissolution profiles of the specimens before and after storage were measured twice in 0.1 mol/L aqueous hydrochloric acid solution. Dissolution rate was evaluated using the absorbance measurement method described in the section on Dissolution Test Method. The results are shown in Tables 5 to 8 as the average values of the dissolution rates.

TABLE 5

| Specimen | Storage Period | Dissolution Rate (%) | | | | |
|---|---|---|---|---|---|---|
| | | 5 min | 10 min | 15 min | 20 min | 30 min |
| Example 1 | Initial | 40 | 74 | 95 | 100 | 100 |
| | 2 weeks | 37 | 68 | 91 | 100 | 101 |
| | 1 month | 37 | 66 | 87 | 99 | 100 |
| Example 2 | Initial | 44 | 76 | 96 | 98 | 98 |
| | 2 weeks | 42 | 75 | 97 | 100 | 100 |
| | 1 month | 44 | 78 | 97 | 98 | 98 |
| Example 3 | Initial | 37 | 71 | 96 | 99 | 100 |
| | 2 weeks | 36 | 67 | 88 | 100 | 101 |
| | 1 month | 38 | 69 | 91 | 98 | 98 |
| Example 4 | Initial | 40 | 75 | 96 | 100 | 100 |
| | 2 weeks | 39 | 69 | 89 | 100 | 101 |
| | 1 month | 37 | 64 | 87 | 97 | 99 |
| Comp. Ex. 1 | Initial | 41 | 77 | 96 | 99 | 100 |
| | 2 weeks | 29 | 51 | 68 | 81 | 96 |
| | 1 month | 22 | 37 | 50 | 61 | 80 |
| Comp. Ex. 2 | Initial | 39 | 71 | 92 | 101 | 102 |
| | 2 weeks | 29 | 52 | 71 | 84 | 99 |
| | 1 month | 27 | 49 | 66 | 79 | 95 |

TABLE 6

| Specimen | Storage Period | Dissolution Rate (%) | | | | |
|---|---|---|---|---|---|---|
| | | 5 min | 10 min | 15 min | 20 min | 30 min |
| Example 5 | Initial | 41 | 71 | 90 | 99 | 102 |
| | 2 weeks | 38 | 67 | 86 | 97 | 104 |
| | 1 month | 38 | 64 | 83 | 95 | 102 |
| Example 6 | Initial | 48 | 84 | 101 | 102 | 103 |
| | 2 weeks | 48 | 81 | 96 | 103 | 103 |
| | 1 month | 40 | 70 | 89 | 98 | 101 |
| Example 7 | Initial | 65 | 96 | 100 | 100 | 100 |
| | 2 weeks | 55 | 98 | 104 | 104 | 104 |
| | 1 month | 69 | 99 | 100 | 100 | 100 |
| Example 8 | Initial | 57 | 98 | 99 | 100 | 100 |
| | 2 weeks | 41 | 77 | 99 | 101 | 101 |
| | 1 month | 36 | 69 | 91 | 99 | 100 |
| Example 9 | Initial | 82 | 99 | 99 | 100 | 100 |
| | 2 weeks | 73 | 97 | 100 | 101 | 101 |
| | 1 month | 33 | 62 | 75 | 83 | 91 |
| Example 10 | Initial | 71 | 101 | 103 | 102 | 103 |
| | 2 weeks | 57 | 98 | 103 | 103 | 103 |
| | 1 month | 41 | 89 | 102 | 102 | 102 |

TABLE 6-continued

| Specimen | Storage Period | Dissolution Rate (%) | | | | |
|---|---|---|---|---|---|---|
| | | 5 min | 10 min | 15 min | 20 min | 30 min |
| Example 11 | Initial | 59 | 95 | 101 | 102 | 102 |
| | 2 weeks | 43 | 75 | 98 | 104 | 105 |
| | 1 month | 43 | 89 | 100 | 101 | 101 |

TABLE 7

| Specimen | Storage Period | Dissolution Rate (%) | | | | |
|---|---|---|---|---|---|---|
| | | 5 min | 10 min | 15 min | 20 min | 30 min |
| Example 12 | Initial | 40 | 72 | 90 | 99 | 102 |
| | 2 weeks | 40 | 71 | 89 | 99 | 104 |
| | 1 month | 38 | 67 | 86 | 97 | 102 |
| Example 13 | Initial | 44 | 76 | 96 | 101 | 101 |
| | 2 weeks | 42 | 75 | 93 | 101 | 103 |
| | 1 month | 42 | 72 | 89 | 98 | 101 |
| Example 14 | Initial | 61 | 96 | 102 | 102 | 102 |
| | 2 weeks | 66 | 102 | 103 | 103 | 104 |
| | 1 month | 52 | 93 | 102 | 102 | 102 |
| Example 15 | Initial | 46 | 89 | 102 | 102 | 102 |
| | 2 weeks | 39 | 71 | 90 | 102 | 103 |
| | 1 month | 37 | 66 | 85 | 98 | 102 |
| Example 16 | Initial | 84 | 97 | 98 | 98 | 98 |
| | 2 weeks | 71 | 99 | 100 | 100 | 100 |
| | 1 month | 28 | 55 | 68 | 76 | 83 |
| Example 17 | Initial | 71 | 99 | 101 | 101 | 101 |
| | 2 weeks | 44 | 90 | 101 | 101 | 101 |
| | 1 month | 39 | 85 | 100 | 100 | 100 |
| Example 18 | Initial | 59 | 96 | 100 | 101 | 101 |
| | 2 weeks | 55 | 95 | 102 | 103 | 103 |
| | 1 month | 52 | 93 | 100 | 101 | 101 |

TABLE 8

| Specimen | Storage Period | Dissolution Rate (%) | | | | |
|---|---|---|---|---|---|---|
| | | 5 min | 10 min | 15 min | 20 min | 30 min |
| Comp. Ex. 3 | Initial | 48 | 89 | 98 | 99 | 99 |
| | 2 weeks | 27 | 50 | 69 | 83 | 98 |
| | 1 month | 26 | 49 | 67 | 81 | 96 |
| Comp. Ex. 4 | Initial | 78 | 102 | 102 | 102 | 102 |
| | 2 weeks | 30 | 57 | 76 | 91 | 101 |
| | 1 month | 27 | 53 | 73 | 88 | 102 |
| Comp. Ex. 5 | Initial | 61 | 95 | 100 | 100 | 100 |
| | 2 weeks | 27 | 50 | 65 | 77 | 93 |
| | 1 month | 31 | 54 | 69 | 81 | 96 |

Example 19

4.5 g of Pharmacological Compound 1, 394.0 g of lactose (DFE Pharma) and 49.5 g of low-substituted hydroxypropyl cellulose (LH21, Shin-Etsu Chemical Co., Ltd.) were mixed with a stirring granulator. 14.9 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 6.5 mm and mass of 110 mg.

The resulting tablets were coated with a water-soluble film using hypromellose-based Opadry Pink (containing propylene glycol, Colorcon Japan LLC) to obtain film-coated tablets (coating amount: 7 mg/tablet).

Example 20

120.0 g of Pharmacological Compound 1, 2005.2 g of lactose (DFE Pharma) and 264.0 g of low-substituted hydroxypropyl cellulose (LH21, Shin-Etsu Chemical Co., Ltd.) were mixed with a stirring granulator. 79.2 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 6.5 mm and mass of 110 mg.

The resulting tablets were coated with a water-soluble film using hypromellose-based Opadry Red (not containing propylene glycol, Colorcon Japan LLC) and propylene glycol (Adeka Corporation) to obtain film-coated tablets (coating amount: 7 mg/tablet, mass ratio of Opadry Red to propylene glycol=9:1).

Example 21

240.0 g of Pharmacological Compound 1, 1885.2 g of lactose (DFE Pharma) and 264.0 g of low-substituted hydroxypropyl cellulose (LH21, Shin-Etsu Chemical Co., Ltd.) were mixed with a stirring granulator. 79.2 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 6.5 mm and mass of 110 mg.

The resulting tablets were coated with a water-soluble film using hypromellose-based Opadry Red (not containing propylene glycol, Colorcon Japan LLC) and propylene glycol to obtain film-coated tablets (coating amount: 7 mg/tablet, mass ratio of Opadry Red to propylene glycol=9:1).

Example 22

67.5 g of Pharmacological Compound 1, 331.0 g of lactose (DFE Pharma) and 49.5 g of low-substituted hydroxypropyl cellulose (LH21, Shin-Etsu Chemical Co., Ltd.) were mixed with a stirring granulator. 14.9 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 6.5 mm and mass of 110 mg.

The resulting tablets were coated with a water-soluble film using hypromellose-based Opadry Pink (containing propylene glycol, Colorcon Japan LLC) to obtain film-coated tablets (coating amount: 7 mg/tablet).

Example 23

600.0 g of Pharmacological Compound 1, 1525.2 g of lactose (DFE Pharma) and 264.0 g of low-substituted hydroxypropyl cellulose (LH21, Shin-Etsu Chemical Co., Ltd.) were mixed with a stirring granulator. 79.2 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 6.5 mm and mass of 110 mg.

The resulting tablets were coated with a water-soluble film using hypromellose-based Opadry Red (not containing propylene glycol, Colorcon Japan LLC) and propylene glycol (Adeka Corporation) to obtain film-coated tablets (coating amount: 7 mg/tablet, mass ratio of Opadry Red to propylene glycol=9:1).

Example 24

225.0 g of Pharmacological Compound 1, 173.5 g of lactose (DFE Pharma) and 49.5 g of low-substituted hydroxypropyl cellulose (LH21, Shin-Etsu Chemical Co., Ltd.) were mixed with a stirring granulator. 14.9 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 6.5 mm and mass of 110 mg.

The resulting tablets were coated with a water-soluble film using hypromellose-based Opadry Pink (containing propylene glycol, Colorcon Japan LLC) to obtain film-coated tablets (coating amount: 7 mg/tablet).

Example 25

225.0 g of Pharmacological Compound 1, 173.5 g of lactose (DFE Pharma) and 49.5 g of low-substituted hydroxypropyl cellulose (LH21, Shin-Etsu Chemical Co., Ltd.) were mixed with a stirring granulator. 14.9 g of hydroxypropyl cellulose (SL, Nippon Soda Co., Ltd.) dissolved in a suitable amount of aqueous ethanol solution (35 w/w %) were added to the resulting mixture followed by subjecting to granulation with a stirring granulator. After drying the resulting granules using a fluidized bed, the granules were sized using a screen having an opening diameter of 1 mm.

5.0 g of low-substituted hydroxypropyl cellulose (LH21, Shin-Etsu Chemical Co., Ltd.) and 1.5 g of sodium stearyl fumarate (JRS Pharma) were added and mixed per 93.5 g of sized granules. The resulting mixture was compressed using a rotary tableting machine to obtain tablets having a diameter of 8.0 mm and mass of 220 mg.

The resulting tablets were coated with a water-soluble film using hypromellose-based Opadry Pink (containing propylene glycol, Colorcon Japan LLC) to obtain film-coated tablets (coating amount: 11 mg/tablet).

[Dissolution Test Result 2]

The specimens prepared in Examples 19 to 25 were placed in vials and stored for 1 month at 60° C. and 75% relative humidity under conditions of being open to the atmosphere and under protection from light. The dissolution profiles of the specimens before and after storage were measured in 0.1 mol/L aqueous hydrochloric acid solution. Dissolution rate in Example 19 was evaluated using the high-performance liquid chromatography method described in the section on Dissolution Test Method. Dissolution rates in Examples 20 to 25 were evaluated using the absorbance measurement method described in the section on Dissolution Test Method. The dissolution profiles in Examples 19, 24 and 25 were measured 3 times, while the dissolution profiles in Examples 20 to 23 were measured 6 times. The results are shown in Table 10 as the average values of the dissolution rates.

TABLE 10

| Specimen | Storage Period | Dissolution Rate (%) | | | | |
|---|---|---|---|---|---|---|
| | | 5 min | 10 min | 15 min | 20 min | 30 min |
| Example 19 | Initial | 70 | 89 | 91 | 91 | 91 |
| | 1 month | 59 | 86 | 89 | 90 | 90 |
| Example 20 | Initial | 65 | 99 | 100 | 100 | 100 |
| | 1 month | 84 | 98 | 98 | 99 | 99 |
| Example 21 | Initial | 26 | 86 | 96 | 98 | 99 |
| | 1 month | 60 | 97 | 98 | 98 | 98 |
| Example 22 | Initial | 34 | 93 | 94 | 94 | 94 |
| | 1 month | 47 | 92 | 95 | 95 | 95 |
| Example 23 | Initial | 26 | 83 | 98 | 99 | 99 |
| | 1 month | 37 | 93 | 98 | 98 | 98 |
| Example 24 | Initial | 26 | 83 | 97 | 97 | 97 |
| | 1 month | 37 | 94 | 97 | 97 | 97 |
| Example 25 | Initial | 32 | 88 | 97 | 96 | 97 |
| | 1 month | 28 | 84 | 96 | 96 | 96 |

Example 26 and Comparative Examples 6 to 9

Tablets having a diameter of 6.5 mm and mass of 110 mg were obtained using the same method as Example 1 so as to have the formulations indicated in Table 11.

Table 11 indicates the constituent amounts of each component per tablet. Those raw materials used that were not described in Example 1 are indicated below.

Cetylpyridinium chloride (Wako Pure Chemical Industries, Ltd.), stearyl alcohol (Kolliwax SA, BASF SE), refined soybean lecithin (Basis LP-2013, The Nisshin OilliO Group, Ltd.), glycerin fatty acid ester (P-100, Riken Vitamin Co., Ltd.), sorbitan fatty acid ester (Nikkol SS-10MV, Nikko Chemicals Co., Ltd.).

TABLE 9

| | Component | Example 19 | Example 20 | Example 21 | Example 22 | Example 23 | Example 24 | Example 25 |
|---|---|---|---|---|---|---|---|---|
| Inside Granules | Pharmacological Compound 1 | 1.0 mg | 5.0 mg | 10.0 mg | 15.0 mg | 25.0 mg | 50.0 mg | 100.0 mg |
| | Lactose | 87.55 mg | 83.55 mg | 78.55 mg | 73.55 mg | 63.55 mg | 38.55 mg | 77.1 mg |
| | Low-substituted hydroxypropyl cellulose | 11.0 mg | 11.0 mg | 11.0 mg | 11.0 mg | 11.0 mg | 11.0 mg | 22.0 mg |
| | Hydroxypropyl cellulose | 3.3 mg | 3.3 mg | 3.3 mg | 3.3 mg | 3.3 mg | 3.3 mg | 6.6 mg |
| Outside Granules | Low-substituted hydroxypropyl cellulose | 5.5 mg | 5.5 mg | 5.5 mg | 5.5 mg | 5.5 mg | 5.5 mg | 11.0 mg |
| | Sodium stearyl fumarate | 1.65 mg | 1.65 mg | 1.65 mg | 1.65 mg | 1.65 mg | 1.65 mg | 3.3 mg |
| Coating | Opadry Red | — | 6.3 mg | 6.3 mg | — | 6.3 mg | — | — |
| | Opadry Pink | 7.0 mg | — | — | 7.0 mg | — | 7.0 mg | 11.0 mg |
| | Propylene glycol | — | 0.7 mg | 0.7 mg | — | 0.7 mg | — | — |
| | Total | 117 mg | 117 mg | 117 mg | 117 mg | 117 mg | 117 mg | 231 mg |

TABLE 11

| | Component | Example 26 | Comp. Ex. 6 | Comp. Ex. 7 | Comp. Ex. 8 | Comp. Ex. 9 |
|---|---|---|---|---|---|---|
| Inside Granules | Pharmacological Compound 1 | 50.0 mg | 50.0 mg | 50.0 mg | 50.0 mg | 50.0 mg |
| | Lactose | 45.7 mg | 45.7 mg | 45.7 mg | 45.7 mg | 45.7 mg |
| | Low-substituted hydroxypropyl cellulose | 6.6 mg | 6.6 mg | 6.6 mg | 6.6 mg | 6.6 mg |
| | Hydroxypropyl cellulose | 3.3 mg | 3.3 mg | 3.3 mg | 3.3 mg | 3.3 mg |
| Outside Granules | Low-substituted hydroxypropyl cellulose | 3.3 mg | 3.3 mg | 3.3 mg | 3.3 mg | 3.3 mg |
| | Cetylpyridinium chloride | 1.1 mg | — | — | — | — |
| | Stearyl alcohol | — | 1.1 mg | — | — | — |
| | Refined soybean lecithin | — | — | 1.1 mg | — | — |
| | Glycerin fatty acid ester | — | — | — | 1.1 mg | — |
| | Sorbitan fatty acid ester | — | — | — | — | 1.1 mg |
| | Total | 110 mg | 110 mg | 110 mg | 110 mg | 110 mg |

[Dissolution Test Result 3]

The specimens prepared in Example 26 and Comparative Examples 6 to 9 were placed in vials and stored for 2 weeks and 1 month at 60° C. and 75% relative humidity under conditions of being open to the atmosphere and under protection from light. The dissolution profiles of the specimens before and after storage were measured twice in 0.1 mol/L aqueous hydrochloric acid solution. Dissolution rates were evaluated using the absorbance measurement method described in the section on Dissolution Test Method. The results are shown in Table 12 as the average values of the dissolution rates.

TABLE 12

| | | Dissolution Rate (%) | | | | |
|---|---|---|---|---|---|---|
| Specimen | Storage Period | 5 min | 10 min | 15 min | 20 min | 30 min |
| Example 26 | Initial | 43 | 77 | 97 | 101 | 101 |
| | 2 weeks | 46 | 81 | 96 | 102 | 103 |
| | 1 month | 55 | 90 | 100 | 100 | 100 |
| Comp. Ex. 6 | Initial | 43 | 80 | 98 | 100 | 100 |
| | 2 weeks | 22 | 42 | 60 | 72 | 90 |
| | 1 month | 22 | 40 | 56 | 69 | 88 |
| Comp. Ex. 7 | Initial | 42 | 85 | 99 | 100 | 100 |
| | 2 weeks | 30 | 55 | 73 | 88 | 100 |
| | 1 month | 31 | 54 | 74 | 90 | 99 |
| Comp. Ex. 8 | Initial | 47 | 86 | 101 | 103 | 103 |
| | 2 weeks | 20 | 34 | 47 | 61 | 78 |
| | 1 month | 17 | 29 | 42 | 54 | 71 |
| Comp. Ex. 9 | Initial | 52 | 89 | 101 | 101 | 101 |
| | 2 weeks | 21 | 36 | 49 | 59 | 77 |
| | 1 month | 19 | 31 | 45 | 57 | 81 |

Figure 1:
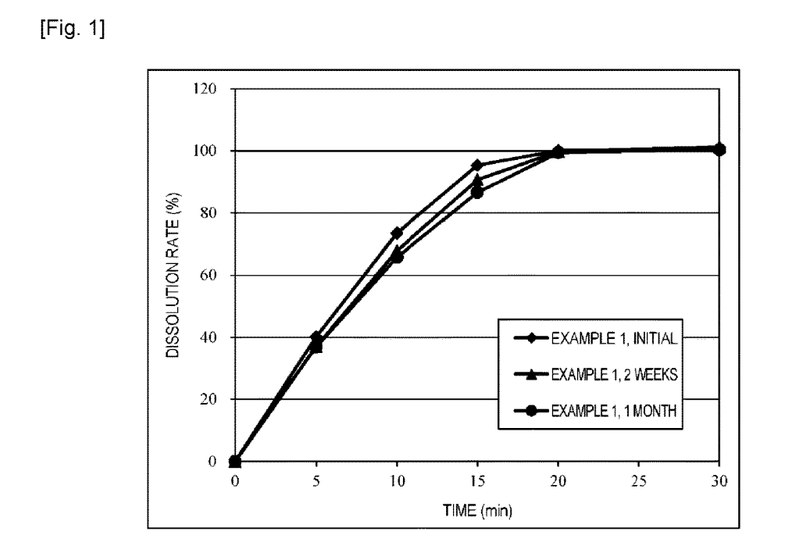
FIG. 1 shows an initial dissolution profile and dissolution profiles after storage for 2 weeks and 1 month at 60° C. and 75% relative humidity under conditions of being open to the atmosphere and under protection from light in a 0.1 mol/L aqueous hydrochloric acid solution of Example 1.
Figure 2:
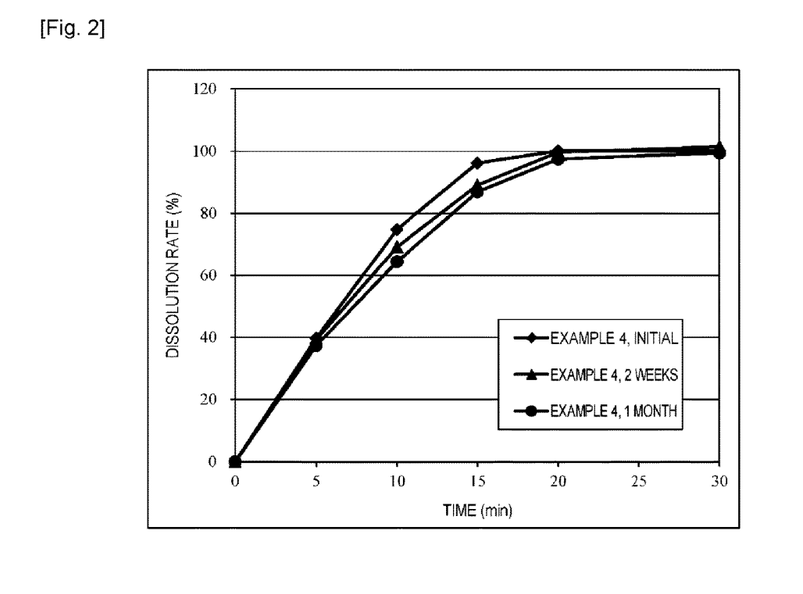
FIG. 2 shows an initial dissolution profile and dissolution profiles after storage for 2 weeks and 1 month at 60° C. and 75% relative humidity under conditions of being open to the atmosphere and under protection from light in a 0.1 mol/L aqueous hydrochloric acid solution of Example 4.
Figure 3:
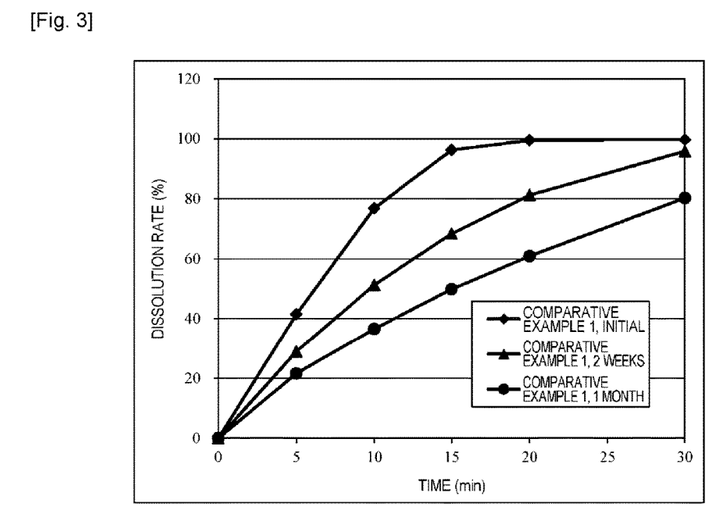
FIG. 3 shows an initial dissolution profile and dissolution profiles after storage for 2 weeks and 1 month at 60° C. and 75% relative humidity under conditions of being open to the atmosphere and under protection from light in a 0.1 mol/L aqueous hydrochloric acid solution of Comparative Example 1.
Figure 4:
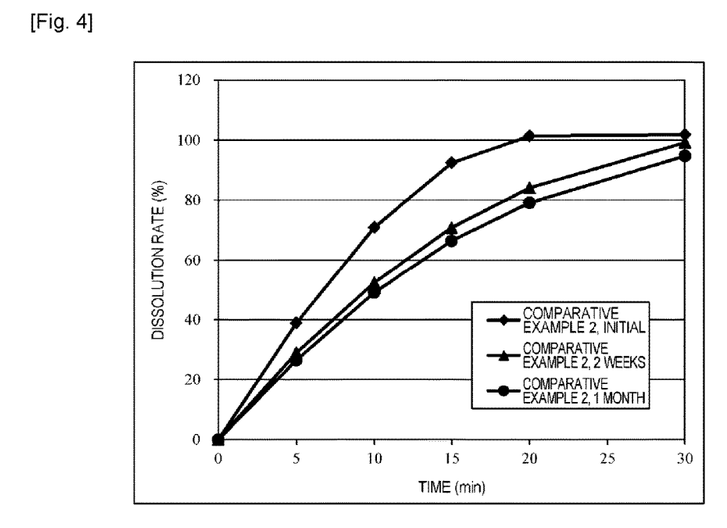
FIG. 4 shows an initial dissolution profile and dissolution profiles after storage for 2 weeks and 1 month at 60° C. and 75% relative humidity under conditions of being open to the atmosphere and under protection from light in a 0.1 mol/L aqueous hydrochloric acid solution of Comparative Example 2.

Changes in dissolution profiles attributable to storage were not observed in Examples 1 and 4 that incorporated a salt of a compound having a C12-22 saturated aliphatic hydrocarbon group in the form of sodium stearyl fumarate or magnesium stearate (FIG. 1 and FIG. 2). On the other hand, considerable delays in the dissolution profiles attributable to storage were observed in Comparative Examples 1 and 2 that incorporated stearic acid or sucrose fatty acid ester, which is not a salt of a compound having a C12-22 saturated aliphatic hydrocarbon group (FIG. 3 and FIG. 4).

15 minute dissolution rates in Examples 1 to 4 and Example 26, which incorporated a salt of a compound having a C12-22 saturated aliphatic hydrocarbon group, were 75% or more throughout the 2 week and 1 month storage periods. On the other hand, 15 minute dissolution rates decreased to below 75% following 2 weeks of storage in the case of Comparative Examples 1 and 2 and Comparative Examples 6 to 9, which incorporated compounds in the manner of stearic acid or fatty acid esters that are not salts of a compound having a C12-22 saturated aliphatic hydrocarbon group.

Figure 5:
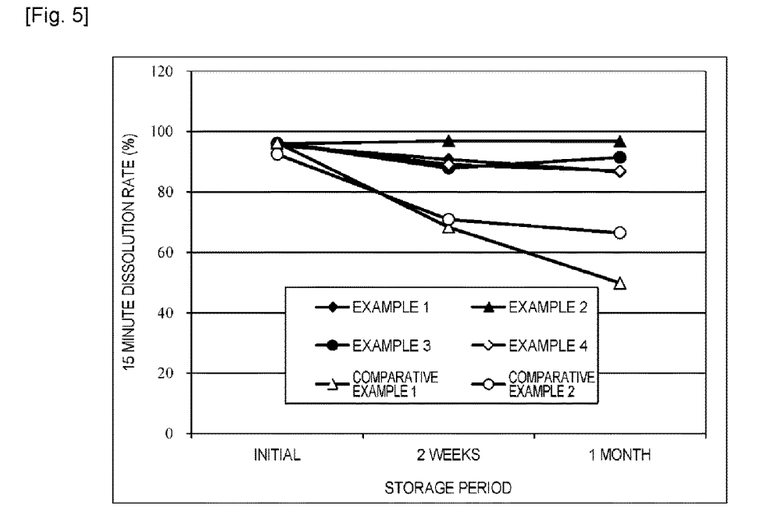
FIG. 5 shows changes in dissolution rates in 15 minutes attributable to storage at 60° C. and 75% relative humidity under conditions of being open to the atmosphere and under protection from light among salts of compounds having a C12-22 saturated aliphatic hydrocarbon group. Each samples further contains a low-substituted hydroxypropyl cellulose.
Figure 6:
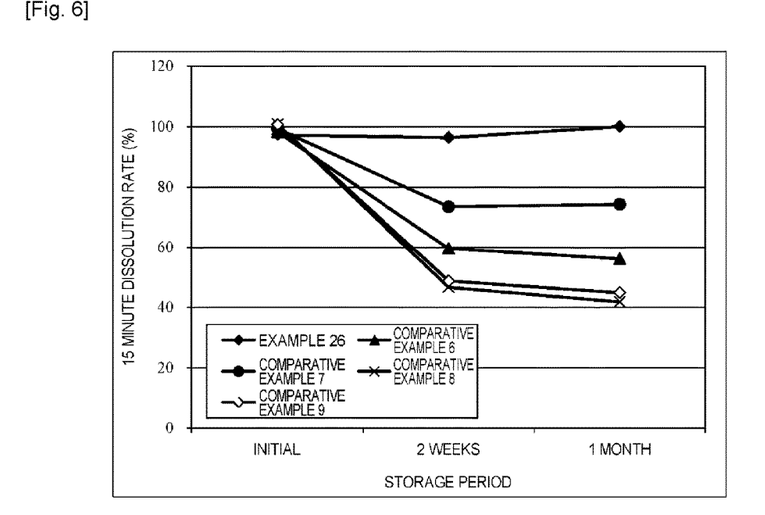
FIG. 6 shows changes in dissolution rates in 15 minutes attributable to storage at 60° C. and 75% relative humidity under conditions of being open to the atmosphere and under protection from light among salts of compounds having a C12-22 saturated aliphatic hydrocarbon group in the same manner as FIG. 5. Each samples further contains a low-substituted hydroxypropyl cellulose.

Incorporation of a salt of a compound having a C12-22 saturated aliphatic hydrocarbon group is shown to be able to inhibit delays in dissolution attributable to storage of a preparation containing Pharmacological Compound 1 (FIG. 5 and FIG. 6).

15 minute dissolution rates in Examples 8, 15, 10, 17, 11 and 18, which incorporated a salt of a compound having a C12-22 saturated aliphatic hydrocarbon group, were 75% or more throughout the 2 week and 1 month storage periods. On the other hand, 15 minute dissolution rates decreased to about 70% following 1 month of storage in the case of Comparative Examples 3 to 5, which incorporated compounds that are not a salt of a compound having a C12-22 saturated aliphatic hydrocarbon group.

Figure 7:
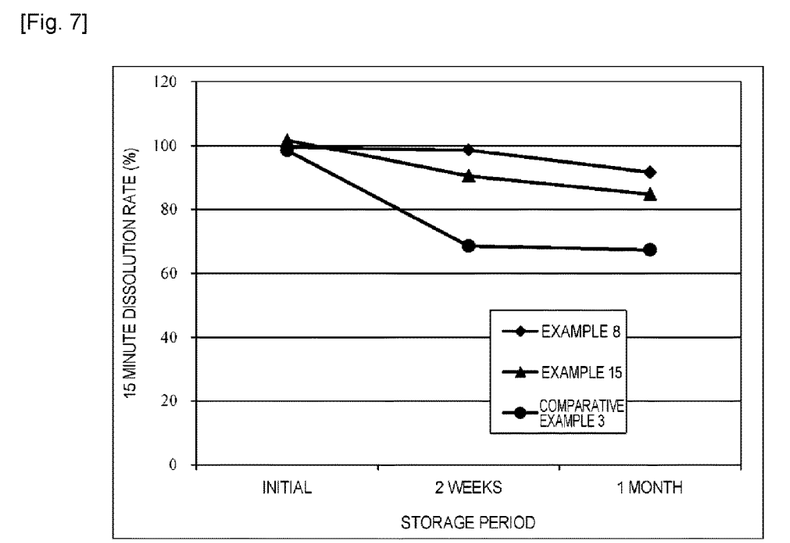
FIG. 7 shows changes in dissolution rates in 15 minutes attributable to storage at 60° C. and 75% relative humidity under conditions of being open to the atmosphere and under protection from light among salts of compounds having a C12-22 saturated aliphatic hydrocarbon group. Each samples further contains carmellose calcium.
Figure 8:
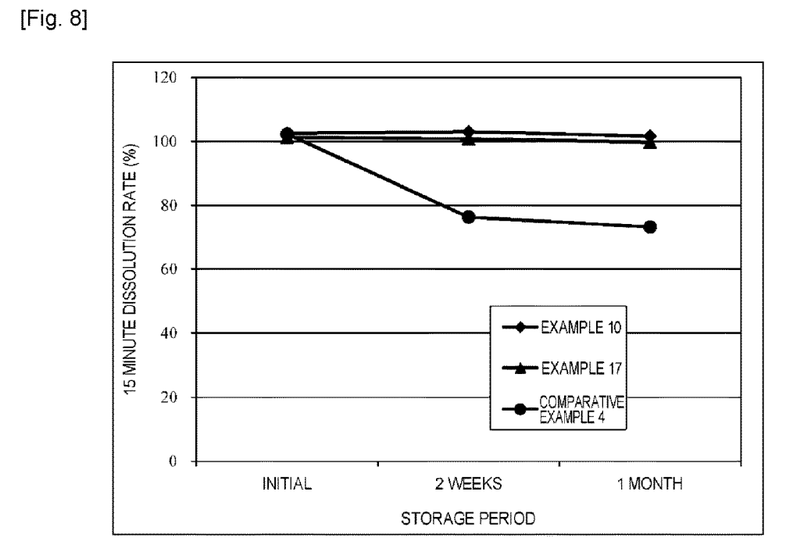
FIG. 8 shows changes in dissolution rates in 15 minutes attributable to storage at 60° C. and 75% relative humidity under conditions of being open to the atmosphere and under protection from light among salts of compounds having a C12-22 saturated aliphatic hydrocarbon group. Each samples further contains sodium carboxymethyl starch.
Figure 9:
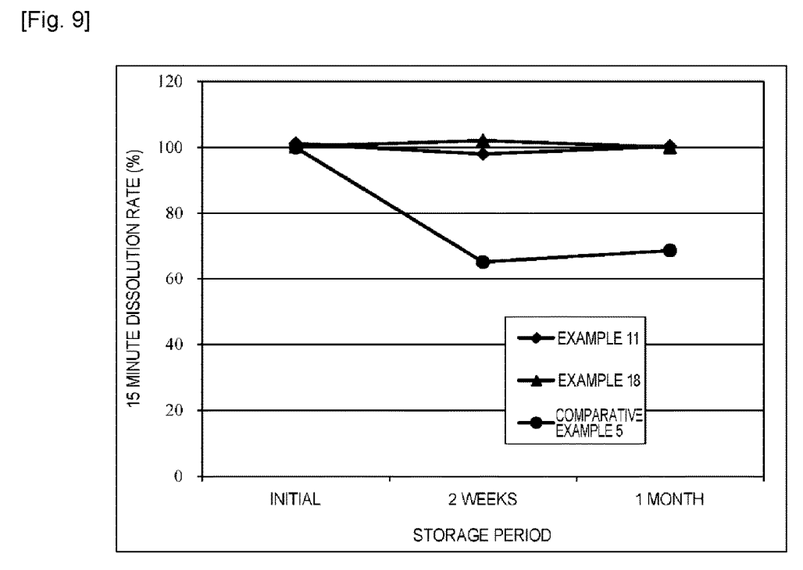
FIG. 9 shows changes in dissolution rates in 15 minutes attributable to storage at 60° C. and 75% relative humidity under conditions of being open to the atmosphere and under protection from light among salts of compounds having a C12-22 saturated aliphatic hydrocarbon group. Each samples further contains carmellose.

Incorporation of a salt of a compound having a C12-22 saturated aliphatic hydrocarbon group is shown to be able to inhibit delays in dissolution attributable to storage of a preparation containing Pharmacological Compound 1 (FIG. 7 to FIG. 9).

[Effect of Content of Pharmacological Compound 1]

Examples 19 to 25 are specimens having different contents of Pharmacological Compound 1, and each of these examples contains sodium stearyl fumarate. The following describes the effect of the content of Pharmacological Compound 1 on dissolution profile based on Dissolution Test Result 2.

Figure 10:
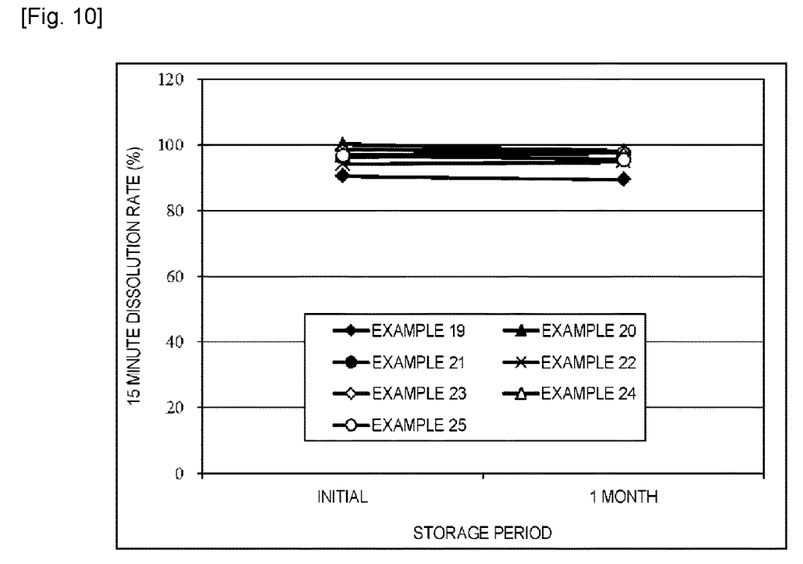
FIG. 10 shows changes in dissolution rates in 15 minutes attributable to storage at 60° C. and 75% relative humidity under conditions of being open to the atmosphere and under protection from light among specimens having different contents of Pharmacological Compound 1.
Figure 11:
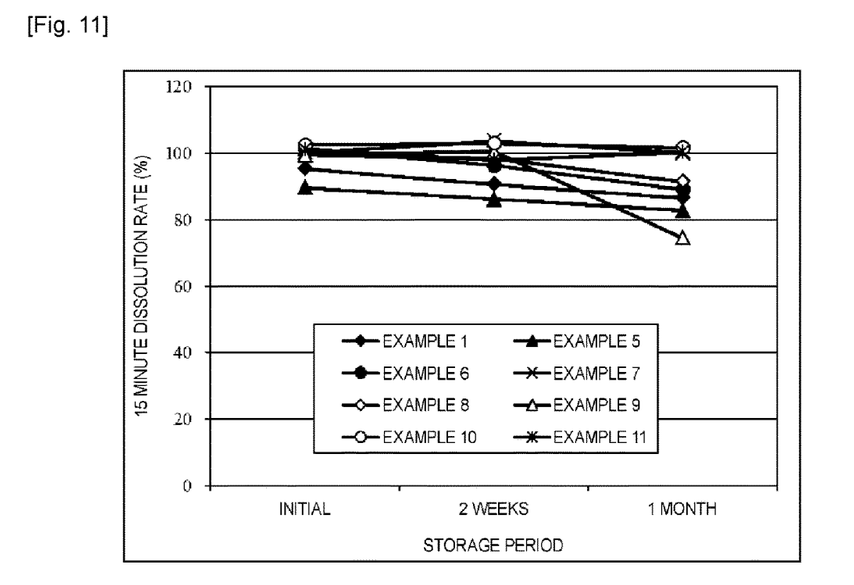
FIG. 11 shows changes in dissolution rates in 15 minutes attributable to storage at 60° C. and 75% relative humidity under conditions of being open to the atmosphere and under protection from light among specimens in which other additives differ when the salt of a compound having a C12-22 saturated aliphatic hydrocarbon group is sodium stearyl fumarate.
Figure 12:
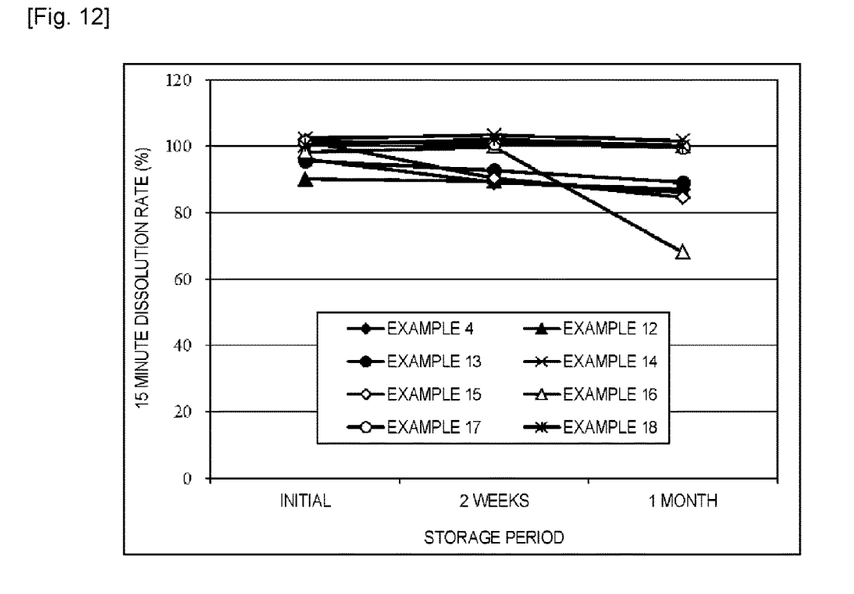
FIG. 12 shows changes in dissolution rates in 15 minutes attributable to storage at 60° C. and 75% relative humidity under conditions of being open to the atmosphere and under protection from light among specimens in which other additives differ when the salt of a compound having a C12-22 saturated aliphatic hydrocarbon group is magnesium stearate.

The effect of storage at 60° C. and 75% relative humidity under conditions of being open to the atmosphere and under protection from light on dissolution rate 15 minutes after the start of the dissolution test is shown in FIG. 10. In the case of using sodium stearyl fumarate, dissolution rates after storage for 1 month were 85% or more even if the content of Pharmacological Compound 1 in a single tablet varied within a range of 1 mg to 100 mg (FIG. 10).

The results of this study indicate that the usefulness of an alkaline metal salt of a compound having a C12-22 saturated aliphatic hydrocarbon group in the form of sodium stearyl fumarate is not dependent on the content of Pharmacological Compound 1.

Comparative Examples 10 to 19

Tablets having a diameter of 6.5 mm and the masses shown in Tables 13 and 14 were obtained using the same method as Example 1 so as to have the formulations indicated in Tables 13 and 14.

Tables 13 and 14 indicate the constituent amounts of each component per tablet. Those raw materials used that were not described in Example 1 or Example 26 are indicated below.

Hydrogenated oil (Lubriwax 103, Freund Corporation), Macrogol (Macrogol 6000, Sanyo Chemical Industries, Ltd.).

TABLE 13

| | Component | Comp. Ex. 10 | Example 1 | Example 2 | Example 3 | Example 4 | Example 26 | Comp. Ex. 11 | Comp. Ex. 12 |
|---|---|---|---|---|---|---|---|---|---|
| Inside Granules | Pharmacological Compound 1 | 50.0 mg | 50.0 mg | 50.0 mg | 50.0 mg | 50.0 mg | 50.0 mg | 50.0 mg | 50.0 mg |
| | Lactose | 45.7 mg | 45.7 mg | 45.7 mg | 45.7 mg | 45.7 mg | 45.7 mg | 45.7 mg | 45.7 mg |
| | Low-substituted hydroxypropyl cellulose | 6.6 mg | 6.6 mg | 6.6 mg | 6.6 mg | 6.6 mg | 6.6 mg | 6.6 mg | 6.6 mg |
| | Hydroxypropyl cellulose | 3.3 mg | 3.3 mg | 3.3 mg | 3.3 mg | 3.3 mg | 3.3 mg | 3.3 mg | 3.3 mg |
| Outside Granules | Low-substituted hydroxypropyl cellulose | 3.3 mg | 3.3 mg | 3.3 mg | 3.3 mg | 3.3 mg | 3.3 mg | 3.3 mg | 3.3 mg |
| | Sodium stearyl fumarate | — | 1.1 mg | — | — | — | — | — | — |
| | Sodium lauryl sulfate | — | — | 1.1 mg | — | — | — | — | — |
| | Calcium stearate | — | — | — | 1.1 mg | — | — | — | — |
| | Magnesium stearate | — | — | — | — | 1.1 mg | — | — | — |
| | Cetylpyridinium chloride | — | — | — | — | — | 1.1 mg | — | — |
| | Hydrogenated oil | — | — | — | — | — | — | 1.1 mg | — |
| | Macrogol | — | — | — | — | — | — | — | 1.1 mg |
| | Total | 108.9 mg | 110 mg | 110 mg | 110 mg | 110 mg | 110 mg | 110 mg | 110 mg |
| | Appearance of Tablet Surface | x (sticking) | ⊗ (no problem) | ⊗ (no problem) | ⊗ (no problem) | ⊗ (no problem) | ⊗ (no problem) | x (sticking) | x (sticking) |

TABLE 14

| | Component | Comp. Ex. 13 | Comp. Ex. 14 | Comp. Ex. 15 | Comp. Ex. 16 | Comp. Ex. 17 | Comp. Ex. 18 | Comp. Ex. 19 |
|---|---|---|---|---|---|---|---|---|
| Inside Granules | Pharmacological Compound 1 | 50.0 mg | 50.0 mg | 50.0 mg | 50.0 mg | 50.0 mg | 50.0 mg | 50.0 mg |
| | Lactose | 45.7 mg | 45.7 mg | 45.7 mg | 45.7 mg | 45.7 mg | 45.7 mg | 45.7 mg |
| | Partially gelatinized starch | 6.6 mg | — | — | — | — | — | — |
| | Cornstarch | — | 6.6 mg | — | — | — | — | — |
| | Crospovidone | — | — | 6.6 mg | — | — | — | — |
| | Carmellose calcium | — | — | — | 6.6 mg | — | — | — |
| | Croscarmellose sodium | — | — | — | — | 6.6 mg | — | — |
| | Sodium carboxymethyl starch | — | — | — | — | — | 6.6 mg | — |
| | Carmellose | — | — | — | — | — | — | 6.6 mg |
| | Hydroxypropyl cellulose | 3.3 mg | 3.3 mg | 3.3 mg | 3.3 mg | 3.3 mg | 3.3 mg | 3.3 mg |
| Outside Granules | Partially gelatinized starch | 3.3 mg | — | — | — | — | — | — |
| | Cornstarch | — | 3.3 mg | — | — | — | — | — |
| | Crospovidone | — | — | 3.3 mg | — | — | — | — |
| | Carmellose calcium | — | — | — | 3.3 mg | — | — | — |
| | Croscarmellose sodium | — | — | — | — | 3.3 mg | — | — |
| | Sodium carboxymethyl starch | — | — | — | — | — | 3.3 mg | — |
| | Carmellose | — | — | — | — | — | — | 3.3 mg |
| | Total | 108.9 mg | 108.9 mg | 108.9 mg | 108.9 mg | 108.9 mg | 108.9 mg | 108.9 mg |
| | Appearance of Tablet Surface | x (sticking) | x (sticking) | x (sticking) | x (sticking) | x (sticking) | x (sticking) | x (sticking) |

[Tablet Surface Observation Results]

The results for observing the tablet surface, when three each of the tablets of Examples 1 to 4, Example 26 and Comparative Examples 10 to 19 were prepared, are shown in Tables 13 and 14.

As a result, the surfaces of the tablets of Comparative Examples 10 to 19, which do not contain a salt of a compound having a C12-22 saturated aliphatic hydrocarbon group in the formulation thereof, demonstrated surface roughness caused by sticking that was unacceptable in terms of appearance. On the other hand, tablets having a smooth surface were obtained in Examples 1 to 4 and Example 26, which contain a salt of a compound having a C12-22 saturated aliphatic hydrocarbon group in the formulation thereof, and were not observed to have any problems in terms of appearance.

[Dissolution Test Result 4]

The specimens prepared in Examples 20 and 23 were placed in vials and stored for 6 months at 40° C. and 75% relative humidity under conditions of being open to the atmosphere and under protection from light. The dissolution profiles of the specimens before and after storage were measured in 0.1 mol/L aqueous hydrochloric acid solution. Dissolution rates in Examples 20 and 23 were evaluated 6 times using the absorbance measurement method described in the section on Dissolution Test Method. The results are shown in Table 15 as the average values of the dissolution rates.

TABLE 15

| | | Dissolution Rate (%) | | | | |
|---|---|---|---|---|---|---|
| Specimen | Storage Period | 5 min | 10 min | 15 min | 20 min | 30 min |
| Example 20 | Initial | 65 | 99 | 100 | 100 | 100 |
| | 3 months | 80 | 95 | 95 | 95 | 95 |
| | 6 months | 76 | 94 | 98 | 98 | 99 |
| Example 23 | Initial | 26 | 83 | 98 | 99 | 99 |
| | 3 months | 45 | 96 | 98 | 98 | 98 |
| | 6 months | 36 | 93 | 97 | 97 | 97 |

[Effect of Storage at 40° C. on Dissolution Behavior]

Examples 20 and 23 are specimens having different contents of Pharmacological Compound 1, and each of these examples contains sodium stearyl fumarate. In the case of using sodium stearyl fumarate, the average dissolution rates at 15 minutes after storage for 6 months at 40° C. and 75% relative humidity under conditions of being open to the atmosphere and under protection from light were 85% or more (Table 15).

The results of this study indicate that an alkaline metal salt of a compound having a C12-22 saturated aliphatic hydrocarbon group in the form of sodium stearyl fumarate is able to inhibit delays in dissolution of a preparation containing Pharmacological Compound 1 even if stored at 40° C.

INDUSTRIAL APPLICABILITY

The present invention demonstrates industrial applicability in the field of pharmaceuticals as a result of being able to provide a stable pharmaceutical composition that does not cause a substantial change in the dissolution profile even after storage for a certain period of time.

What is claimed is:

1. A pharmaceutical composition comprising a compound represented by formula (1):

(1)

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and a salt of a compound having a C12-22 saturated aliphatic hydrocarbon group.

2. The pharmaceutical composition according to claim 1, wherein the salt of a compound having a C12-22 saturated aliphatic hydrocarbon group is at least one selected from the group consisting of a metal salt of a C12-22 saturated aliphatic organic acid, a mono alkaline metal salt of a mono C12-22 alkyl fumarate, and a mono alkaline earth metal salt of a mono C12-22 alkyl fumarate.

3. The pharmaceutical composition according to claim 1, wherein the salt of a compound having a C12-22 saturated aliphatic hydrocarbon group is at least one selected from the group consisting of sodium stearyl fumarate, sodium lauryl sulfate, calcium stearate and magnesium stearate.

4. A pharmaceutical composition comprising a compound represented by formula (1):

(1)

or N-[3-((4aS,5R,7aS)-2-amino-5-methyl-4a,5,7,7a-tetrahydro-4H-furo[3,4-d] [1,3]thiazin-7a-yl)-4-fluorophenyl]-5-difluoromethylpyrazine-2-carboxamide, or a pharmaceutically acceptable salt of the foregoing, and means that does not cause a substantial change in the dissolution profile even after storage for a certain period of time.

* * * * *

UNITED STATES PATENT AND TRADEMARK OFFICE
CERTIFICATE OF CORRECTION

PATENT NO. : 10,117,876 B2
APPLICATION NO. : 15/516567
DATED : November 6, 2018
INVENTOR(S) : Zaima et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 54 days.

Signed and Sealed this
Twenty-fifth Day of June, 2019

Andrei Iancu
*Director of the United States Patent and Trademark Office*